United States Patent [19]
Weiss et al.

[11] Patent Number: 5,792,160
[45] Date of Patent: Aug. 11, 1998

[54] EPITHELIAL REMOVER TOOL

[76] Inventors: Richard A. Weiss, 421 San Bernardino, Newport Beach, Calif. 92663; Burrell E. Clawson, 1411 N. Bayfront, Balboa Island, Calif. 92662

[21] Appl. No.: 785,876

[22] Filed: Jan. 21, 1997

[51] Int. Cl.⁶ ................................................. A61B 17/24
[52] U.S. Cl. ...................................... 606/161; 606/166
[58] Field of Search .............................. 606/1, 4, 5, 107, 606/161, 162, 166, 170, 180, 131, 132

[56] References Cited

U.S. PATENT DOCUMENTS 5,649,943  7/1997  Amoils ............................ 606/161

FOREIGN PATENT DOCUMENTS 0303174  2/1989  European Pat. Off. ............ 606/166
9108711  6/1991  WIPO ................................ 606/166

*Primary Examiner*—Glenn K. Dawson
*Attorney, Agent, or Firm*—Harry G. Weissenberger

[57] ABSTRACT

A scrubber pad for a rotating epithelial removal tool is made of a single piece of substantially rigid plastic which has formed thereon a scrubbing surface equipped with a radial channel or channels to retain cell debris and lubricating fluid. An eccentrically located fluid supply conduit can provide additional fluid and can also serve with the radial channels as a visual centering indicator to the patient. The edges of the scrubbing surface can be undercut to give them a desired flexibility.

7 Claims, 6 Drawing Sheets

EPITHELIAL REMOVER TOOL

FIELD OF THE INVENTION

This invention relates to tools for abrading the epithelial layer of the cornea in eye surgery, and more particularly to an improved tool for removing the epithelial layer prior to laser corneal reshaping.

BACKGROUND OF THE INVENTION

In photo-refractive keratotomy (PRK) laser surgery for the correction of myopia or hyperopia, it is necessary to remove the epithelial layer on the outside of the cornea before surgically shaping the outer surface of the cornea. This procedure has conventionally been done manually with a scalpel, or more recently by a rotating stiff-bristled brush. Although such a brush is effective in removing the epithelium, it has a tendency to become clogged in use with epithelial cells. Also, bristles may come loose or break and scratch or get into the eye, resulting in a less than smooth removal of the epithelial layer.

SUMMARY OF THE INVENTION

The present invention provides an epithelial removal pad which is not subject to clogging, and which leaves the cornea with a smoothly cleared surface. The invention accomplishes this by substituting for the brush in the conventional tool a solid disposable plastic scrubber pad with a concave abrasive surface and built-in, preferably flushable deep channels for the storage of cellular debris as the abrasion proceeds. The flexibility of the scrubber pad may be varied near the edges of the scrubbing surface to provide special abrasion characteristics. A central axial visual indication in the scrubber pad as it rotates over the patient's eye when the doctor lowers the tip into contact with the eye is preferably provided to allow the patient to visually verify the correct alignment of the scrubber before the scrubbing starts.

DESCRIPTION OF THE PREFERRED EMBODIMENTS

Figure 1:
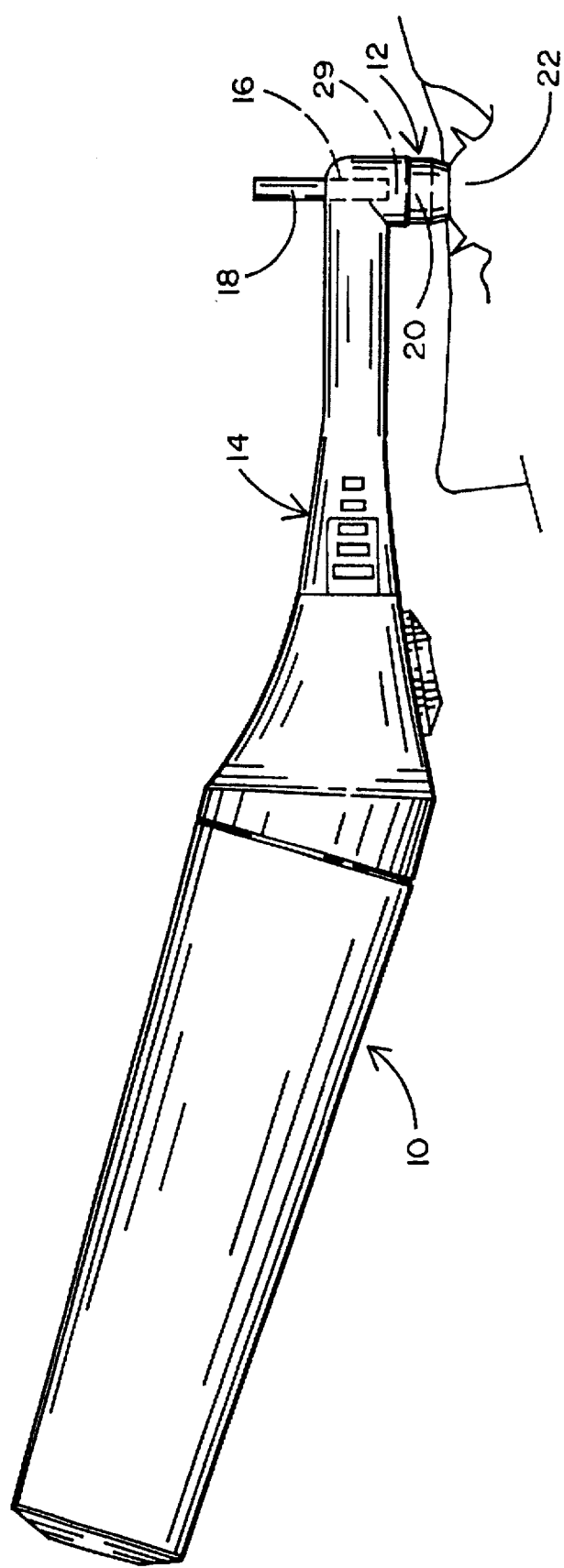
FIG. 1 is a side elevation of a scrubber tool using the scrubber pad of this invention.

FIG. 1 shows the scrubber tool 10 to which a rotating tip 12 can be removably attached. The scrubber tool 10 can be a conventional battery-operated dental hygienist's cleaning tool with a removable right-angle device 14 that drives a hexagonal drive shaft 16. In accordance with the invention, the drive shaft 16 may be hollow and may be connected to a source 18 of a biolubricant such as normal saline solution, for purposes described below.

In accordance with the invention, the rotating tip 12 takes the form of a disposable scrubber pad 20 shown in more detail in FIGS. 2–5. In use, the scrubber pad is applied to a patient's topically anesthetized eye 22. On its front, the scrubber pad 20 carries a concave abrasive scrubbing surface 23, preferably of a similar radius as the patient's epithelium. The rapid rotation of the scrubbing surface by the tool 10 abrades the epithelial layer 24 (FIG. 2) of the eye 22.

Figure 2:
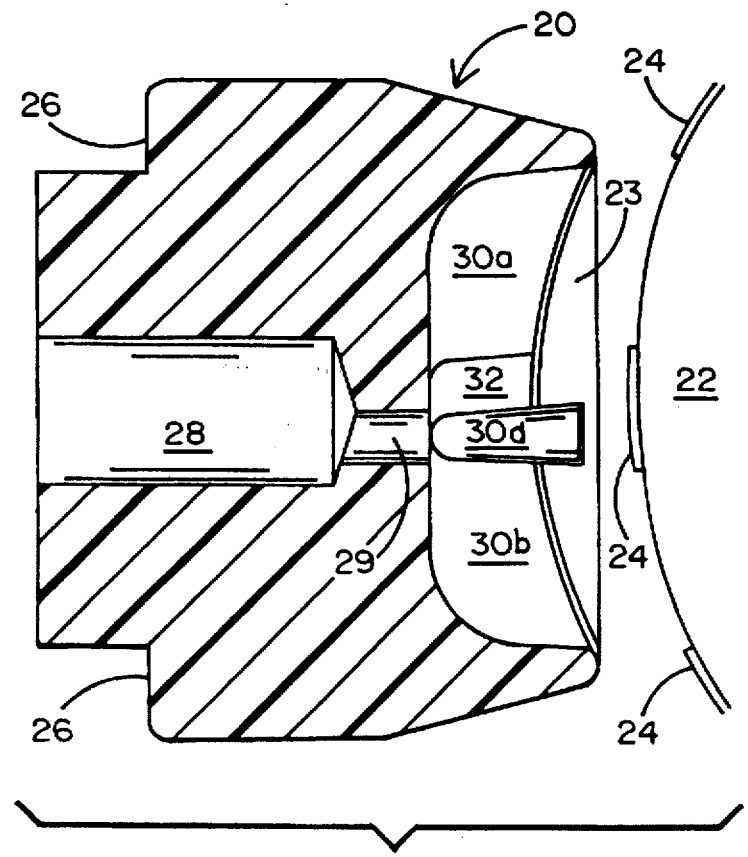
FIG. 2 is a substantially axial cross section of a first embodiment of the scrubber pad and the effect of its use on the eye.

FIG. 2 shows a cross section of a first embodiment of the inventive scrubber pad 20. The pad 20 is formed as a single piece from a hard sterilizable plastic such as PMMA. A hexagonal recess 28 allows the pad 20 to be mounted on the shaft 16. Biolubricant from the hollow shaft 16 can pass by capillary action through the passage 29 to the scrubbing surface 23 and the eye 22. Wide shoulders 26 maintain the pad 20 stably in contact with the head surface of the tool 10 during rotation.

The scrubbing surface 23 has a carefully controlled roughness which is sufficient to break up the epithelial cell surfaces without displacing or imparting scratches to the immediately underlying Bowman's layer of cells. In the basic embodiment of the invention shown in FIG. 2, the scrubbing surface 23 has a closely similar radius of curvature as the eye 22, so that the epithelial layer 24 is uniformly removed throughout the area of interest.

Figure 3A:
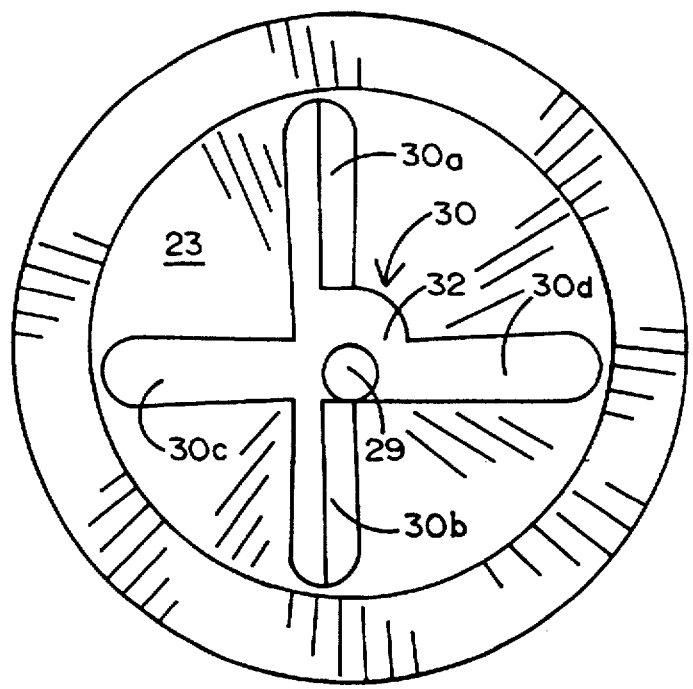
FIGS. 3a–3c are front elevations of three variations of the scrubber embodiment of FIG. 2 useful mainly in hyperopia correction.
Figure 3B:
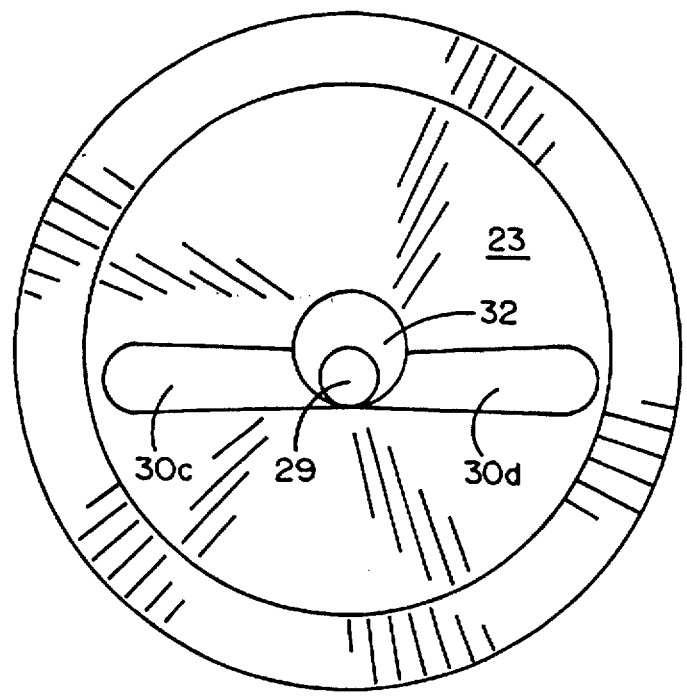
Figure 3C:
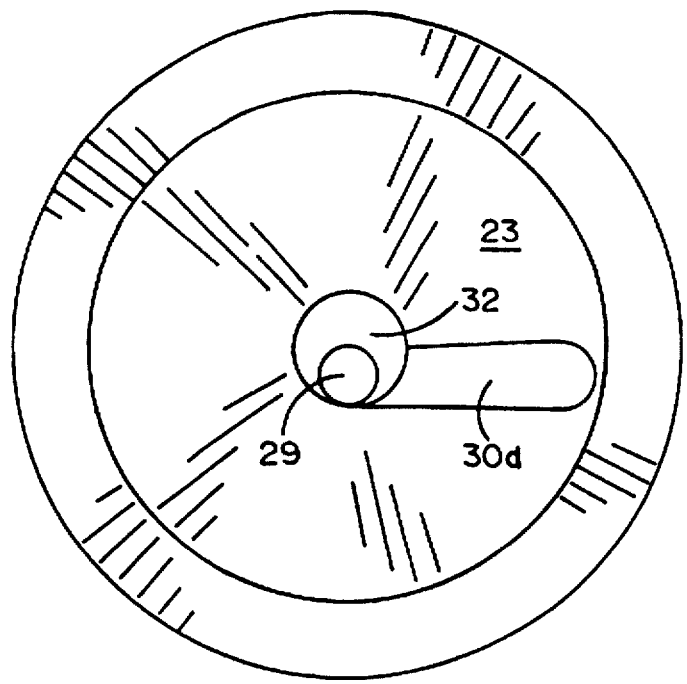

FIGS. 3a–c illustrate several preferred arrangements of the channels or channels 30 which catch the removed epithelial cells and store lubricating fluid such as tears and/or externally supplied lubricating wetting solution. In each of the embodiments of FIGS. 3a–c, a central area 32 coaxial with the axis of rotation of the scrubber pad 20 is deeply recessed so as to leave the central area of the eye 22 untouched. In the treatment of hyperopia, this allows the epithelium to remain intact in the central portion of the eye in which no correction is needed. As a result, regrowth of the epithelial layer is faster and less painful, and patient vision immediately after surgery is improved.

Figure 4C:
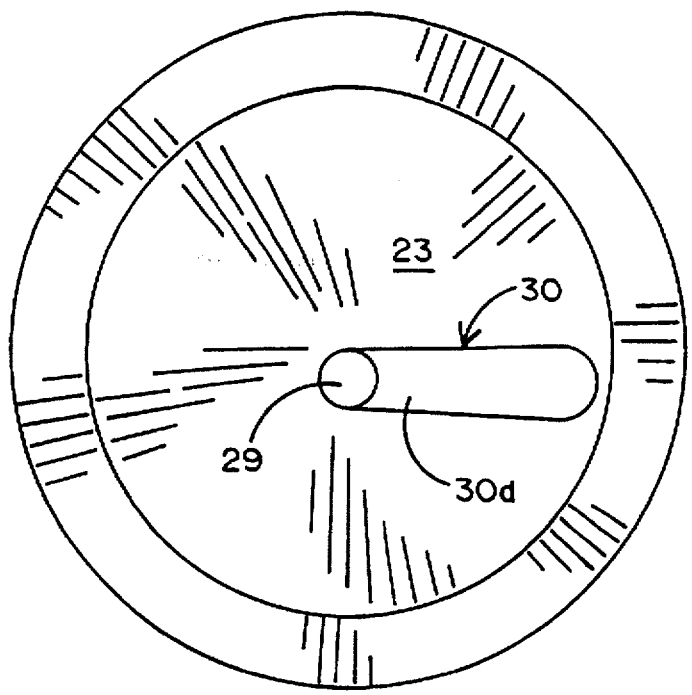
FIGS. 4a–4c are front elevations of three other variations of the scrubber embodiment of FIG. 2 useful in myopia correction.
Figure 4A:
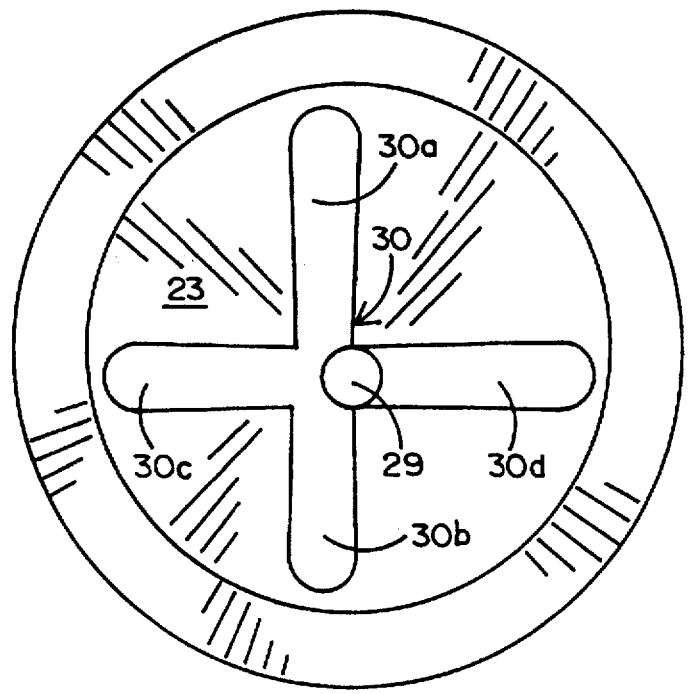
Figure 4B:
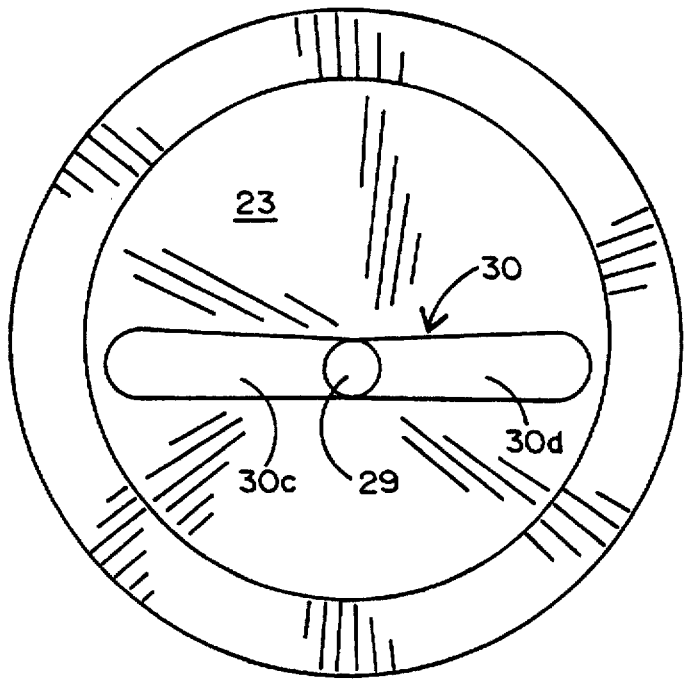

It will be noted in FIGS. 3a–c, as well as in FIGS. 4a–c, that the channels 30 stop short of the periphery of the scrubbing surface 23. The reason for this construction is that it avoids creating sharp edges on the surface of pad 20 which could injure the eyes 22.

FIGS. 4a–c are the same views as FIGS. 3a–c but depict a scrubber 20 for the correction of myopia. In that treatment, the central portion of the eye must also be modified, and therefore the epithelium must be removed throughout the area of interest. An inspection of FIGS. 2 through 5b will show that the lubricant passage 29 which optionally connects the channel 30 with the hollow interior of shaft 16 is eccentrically disposed with respect to the rotational axis 36 of the scrubber pad 20. This assures that the entire epithelium will be contacted by both the scrubbing surface 23 and the lubricating channels 30 at successive times during a revolution of the scrubber pad 20. The same is true of the scrubber pad 20 of FIGS. 3a–c, except that in those figures, the central area of the epithelial layer 24 is never contacted by the scrubbing surface 23.

In the embodiments of FIGS. 3a and 4a, the channel 30 has four segments 30a–d positioned at 90° intervals to provide a maximum of space for containing debris and fluid. Depending upon the particular application of the tool 10, a two-segment channel 30 (FIGS. 3b and 4b) or single-segment channel 30 (FIGS. 3c and 4c) may suffice and thereby provide a larger scrubbing surface for faster action.

Because the rotating passage 29 appears visually different from the surrounding scrubbing surface 23, the rotation of passage 29 about the axis 36 of pad 20 appears to the patient as a reference circle which enables the patient to see, prior to the scrubbing, if the scrubber pad 20 is correctly centered on the eye 22. Thus, the patient is enabled to provide positional feedback to the physician.

Figure 5A:
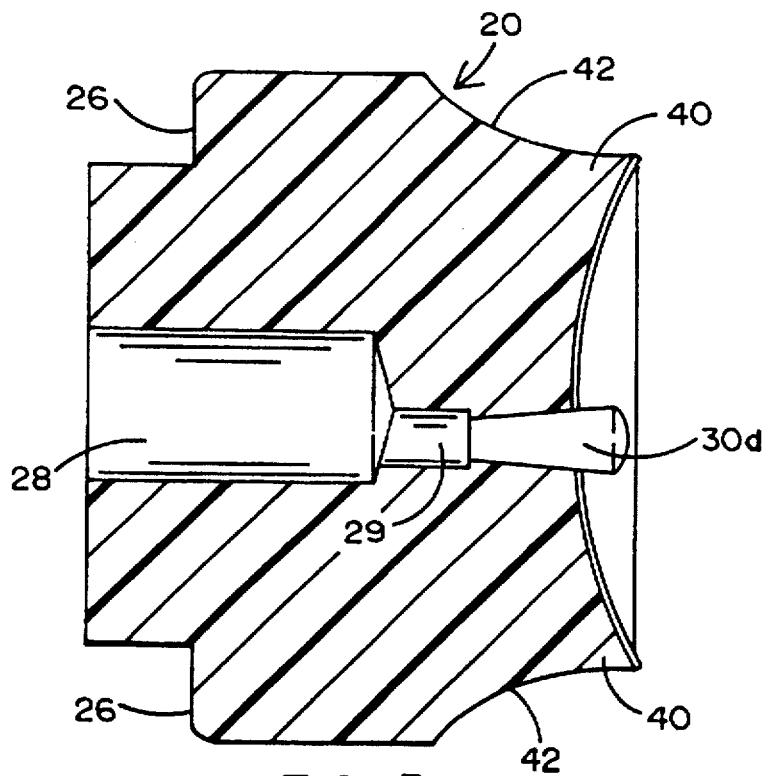
FIGS. 5a and 5b are axial sections of a second embodiment of the inventive scrubber.
Figure 5B:
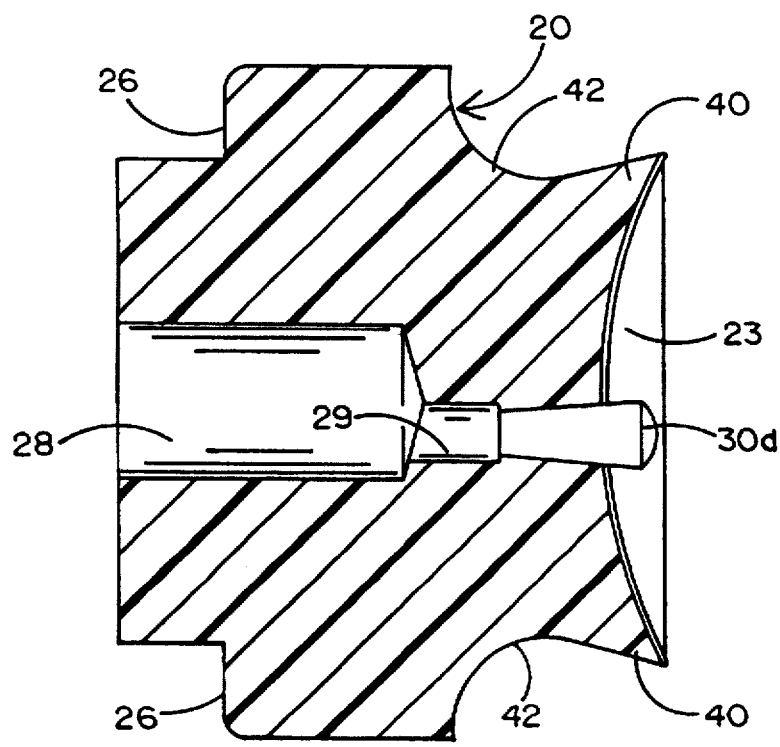

FIGS. 5a and 5b illustrate another embodiment of the invention. Because the eye has a certain degree of resilience, it is sometimes desirable to increase the flexibility of the scrubber pad near the edge of the scrubbing surface. This can be accomplished by undercutting the scrubber pad 10 (which in this instance is made of somewhat elastomeric material) in the vicinity of the scrubbing surface edge 40. FIG. 5a shows a light undercutting of the edge 40 at 42 to make the edge 40 somewhat flexible, while FIG. 5b shows a heavy undercut 42 which makes the edge 40 quite flexible.

It will be seen that the present invention provides a versatile and effective epithelial scrubber. Various modifications and additions may be made to the described embodiments without departing from the spirit and scope of the invention. Thus, other modifications and additions may be obvious to those skilled in the art and may be implemented to adapt the present invention for use in a variety of different applications.

We claim:

1. A scrubber tool for removing epithelium in eye surgery, comprising:
   a) a tool having a shaft, said tool being arranged to rotationally drive said shaft; and
   b) a scrubber pad mounted on said shaft for rotation therewith, said scrubber pad including:
      i) a body; and
      ii a concave scrubbing surface formed on said body;
      iii) the concavity of said surface being substantially equal to the convexity of an eye whose epithelium is to be removed:
      iv said scrubbing surface being sufficiently rough to cause the epithelium to break up and slough off from the underlying tissue layer; and
      v) substantially radial channels being formed in said scrubbing surface to receive cell debris and lubricous fluid retained in said channels by surface tension.

2. The tool of claim 1, in which said channels stop radially short of the outer edge of said scrubbing surface.

3. A scrubber tool for removing epithelium in eye surgery, comprising:
   a) a tool having a shaft, said tool being arranged to rotationally drive said shaft; and
   b) a scrubber pad mounted on said shaft for rotation therewith, said scrubber pad including:
      i) a body; and
      ii a concave scrubbing surface formed on said body;
      iii) the concavity of said surface being substantially equal to the convexity of an eye whose epithelium is to be removed;
      iv said scrubbing surface being sufficiently rough to cause the epithelium to break up and slough off from the underlying tissue layer; and
      v) said shaft including a conduit extending longitudinally through said shaft, said conduit being connected in fluid-transferring relationship with a source of lubricating fluid and with said scrubbing surface.

4. The tool of claim 3, in which fluid is transferred from said lumen to said scrubbing surface by a conduit extending substantially perpendicularly to said scrubbing surface and entering said scrubbing surface eccentrically of the axis of rotation of said scrubbing surface.

5. The tool of claim 4, in which said scrubbing surface has substantially radially extending channels formed therein, and said conduit connects in fluid-transferring relationship with said channels.

6. The tool of claim 3, in which said conduit is positioned to provide to the patient a visual indication of the centering of said scrubbing surface during scrubbing.

7. A scrubber tool for removing epithelium in eye surgery, comprising:
   a) a tool having a shaft, said tool being arranged to rotationally drive said shaft; and
   b) a scrubber pad mounted on said shaft for rotation therewith, said scrubber pad including:
      i) a body; and
      ii a concave scrubbing surface formed on said body;
      iii) the concavity of said surface being substantially equal to the convexity of an eye whose epithelium is to be removed;
      iv said scrubbing surface being sufficiently rough to cause the epithelium to break up and slough off from the underlying tissue layer; and
      v) said scrubber pad being formed of a partially elastomeric material, and the body of said scrubber pad including adjacent the edge of said scrubbing surface a portion having a reduced diameter smaller than the diameter of said scrubbing surface, said reduced diameter being sufficiently smaller than the diameter of said scrubbing surface to provide a selected flexibility for said edge.

\* \* \* \* \*